(12) United States Patent
Nishina et al.

(10) Patent No.: US 10,285,573 B2
(45) Date of Patent: May 14, 2019

(54) ENDOSCOPE HAVING CONDUCTIVE MATERIAL ESTABLISHING ELECTRICAL CONDUCTION BETWEEN BENDING TUBE AND LENS BARREL

(71) Applicant: OLYMPUS CORPORATION, Tokyo (JP)

(72) Inventors: Kenichi Nishina, Hachioji (JP); Tomoaki Ogawa, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/610,685

(22) Filed: Jun. 1, 2017

(65) Prior Publication Data

US 2017/0265715 A1    Sep. 21, 2017

Related U.S. Application Data

(63) Continuation of application No. PCT/JP2016/061796, filed on Apr. 12, 2016.

(30) Foreign Application Priority Data

Jun. 18, 2015 (JP) ................................. 2015-123182

(51) Int. Cl.
*A61B 1/05* (2006.01)
*A61B 1/005* (2006.01)
(Continued)

(52) U.S. Cl.
CPC ............ *A61B 1/005* (2013.01); *A61B 1/0008* (2013.01); *A61B 1/00114* (2013.01); *A61B 1/04* (2013.01);
(Continued)

(58) Field of Classification Search
CPC ....... A61B 1/005; A61B 1/00163; A61B 1/04; A61B 1/0008; A61B 1/05; A61B 1/06;
(Continued)

(56) References Cited

U.S. PATENT DOCUMENTS

| | | | | |
|---|---|---|---|---|
| 4,677,471 A | * | 6/1987 | Takamura | ................ A61B 1/05 348/373 |
| 4,706,654 A | * | 11/1987 | Ogiu | ........................ A61B 1/05 348/E5.026 |

(Continued)

FOREIGN PATENT DOCUMENTS

| CN | 102958421 A | 3/2013 |
|---|---|---|
| CN | 103037749 A | 4/2013 |

(Continued)

OTHER PUBLICATIONS

International Search Report dated Jul. 19, 2016 issued in PCT/JP2016/061796.

(Continued)

*Primary Examiner* — John P Leubecker
(74) *Attorney, Agent, or Firm* — Scully, Scott, Murphy & Presser, P.C.

(57) ABSTRACT

An electronic endoscope of the invention includes: an insertion portion to be inserted into a subject; a distal end rigid portion including a distal end portion and a proximal end portion, the distal end rigid portion being made of resin and provided at a distal end portion of the insertion portion; a bending tube made of metal and provided continuously with the distal end rigid portion; objective optical systems provided at the distal end rigid portion; an image pickup unit that picks up images formed by the objective optical systems; an illumination lens barrel made of metal, the illumination lens barrel holding an illumination optical system provided at the distal end rigid portion and being extended in a direction of the proximal end portion; and a first (Continued)

conductive portion that establishes electrical conduction between the bending tube and the illumination lens barrel.

7 Claims, 13 Drawing Sheets

(51) Int. Cl.
    *A61B 1/04*         (2006.01)
    *G02B 23/24*       (2006.01)
    *H04N 5/225*       (2006.01)
    *A61B 1/00*        (2006.01)

(52) U.S. Cl.
    CPC ....... *G02B 23/243* (2013.01); *G02B 23/2423* (2013.01); *G02B 23/2453* (2013.01); *G02B 23/2469* (2013.01); *H04N 5/2252* (2013.01); *H04N 5/2253* (2013.01); *A61B 1/0011* (2013.01); *A61B 1/00096* (2013.01); *A61B 1/00163* (2013.01)

(58) Field of Classification Search
    CPC .. H04N 5/2252; H04N 5/2253; H04N 5/2254; H04N 5/2256; H04N 2005/2255; G02B 23/243; G02B 23/2453
    See application file for complete search history.

(56) References Cited

U.S. PATENT DOCUMENTS

| | | | | |
|---|---|---|---|---|
| 5,873,816 | A * | 2/1999 | Kagawa | A61B 1/00114 600/110 |
| 6,313,456 | B1 * | 11/2001 | Miyashita | H01L 27/14618 250/208.1 |
| 6,767,322 | B1 * | 7/2004 | Futatsugi | A61B 1/00096 600/129 |
| 8,654,184 | B2 | 2/2014 | Murayama et al. | |
| 2004/0092793 | A1 * | 5/2004 | Akai | A61B 1/05 600/134 |
| 2008/0051634 | A1 * | 2/2008 | Yamashita | A61B 1/00071 600/134 |
| 2008/0266441 | A1 * | 10/2008 | Ichimura | H04N 5/2254 348/340 |
| 2009/0093680 | A1 * | 4/2009 | Tsutsumi | A61B 1/0008 600/140 |
| 2010/0073470 | A1 * | 3/2010 | Takasaki | A61B 1/053 348/76 |
| 2010/0292538 | A1 * | 11/2010 | Hirata | A61B 1/00071 600/129 |
| 2012/0209072 | A1 | 8/2012 | Oue et al. | |
| 2013/0050457 | A1 * | 2/2013 | Murayama | A61B 1/0008 348/75 |
| 2013/0137925 | A1 * | 5/2013 | Ushijima | A61B 1/051 600/109 |
| 2013/0150667 | A1 | 6/2013 | Mitamura et al. | |
| 2014/0296636 | A1 | 10/2014 | Hatano | |

FOREIGN PATENT DOCUMENTS

| | | |
|---|---|---|
| EP | 0 978 251 A1 | 2/2000 |
| EP | 2 561 796 A1 | 2/2013 |
| JP | 2001-221957 A | 8/2001 |
| JP | 2013-198566 A | 10/2013 |
| JP | 2015-039550 A | 3/2015 |
| WO | WO 2012/124526 A1 | 9/2012 |
| WO | WO 2013/035379 A1 | 3/2013 |

OTHER PUBLICATIONS

Extended Supplementary European Search Report dated Jul. 12, 2018 in European Patent Application No. 16 81 1305.8.

* cited by examiner

ENDOSCOPE HAVING CONDUCTIVE MATERIAL ESTABLISHING ELECTRICAL CONDUCTION BETWEEN BENDING TUBE AND LENS BARREL

CROSS REFERENCE TO RELATED APPLICATION

This application is a continuation application of PCT/JP2016/061796 filed on Apr. 12, 2016 and claims benefit of Japanese Application No. 2015-123182 filed in Japan on Jun. 18, 2015, the entire contents of which are incorporated herein by this reference.

BACKGROUND OF THE INVENTION

1. Field of the Invention

The present invention relates to an endoscope in which a metallic lens barrel provided at a distal end rigid portion made of resin and a metallic bending tube are electrically conducted with each other.

2. Description of the Related Art

In recent years, endoscopes to be inserted into a subject have been widely used in medical fields. Observation in a subject is performed with an endoscope by an elongated insertion portion of the endoscope being inserted into the subject. In addition, in general, a rigid member (distal end rigid portion) provided at a distal end of an insertion portion of an endoscope is made of a metal material having conductivity in many cases. In particular, in an endoscope including an insertion portion whose outer diameter is small, a circumference of an image pickup unit is not covered with a metal shield so as to reduce the diameter size of the insertion portion, and a distal end rigid portion is made of metal so as to ensure strength, in many cases.

Therefore, even if static electricity is applied to the distal end rigid portion, the static electricity flows from the distal end rigid portion to the bending tube, and does not leak to the image pickup unit. However, recently, for the purpose of reducing production costs and ensuring voltage endurance in the case where a high-frequency treatment instrument is used with an endoscope, endoscopes including a distal end rigid portion made of resin having an electric insulation property have appeared.

For example, the publication No. WO2012/124526 discloses a technique for preventing a noise from intruding into the image pickup device unit by connecting the metallic connection tube provided at the distal end rigid portion made of resin to the reinforcing barrel provided on the outer circumference of the image pickup device unit, and connecting the reinforcing barrel to the ground portion of the video processor through various kinds of grounding metal members that form a structure of the insertion portion.

In addition, Japanese Patent Application Laid-Open Publication No. 2013-198566 discloses a technique for preventing a noise caused by static electricity, high frequency, or the like from intruding into the image pickup unit, by bringing the channel pipe, which is provided in the distal end rigid portion made of the electric insulation member and grounded, and the device barrel having conductivity of the image pickup unit into surface contact with each other through the conductive member.

SUMMARY OF THE INVENTION

An endoscope according to one aspect of the present invention includes: an insertion portion to be inserted into a subject; a distal end rigid portion including a distal end portion and a proximal end portion, the distal end rigid portion being made of resin and provided at a distal end portion of the insertion portion; a bending tube made of metal and provided continuously with the distal end rigid portion; an objective optical system provided at the distal end rigid portion; an image pickup device that picks up an image formed by the objective optical system; a lens barrel made of metal, the lens barrel holding an illumination optical system provided at the distal end rigid portion, and being extended in a direction of the proximal end portion; and a first conductive portion that establishes electrical conduction between the bending tube and the lens barrel.

DETAILED DESCRIPTION OF THE PREFERRED EMBODIMENT(S)

Hereinafter, embodiments of the present invention will be described based on drawings. Note that each of the drawings is a pattern diagram, and care should be taken to the fact that the relationship between the thicknesses and widths of the respective members, a ratio of the thickness of a certain member to that of another member, and the like are different from the actual ones. It is needless to say that each of the drawings includes a part in which the relationship and ratio among the dimensions are different from those in other drawings.

First Embodiment

Figure 1:
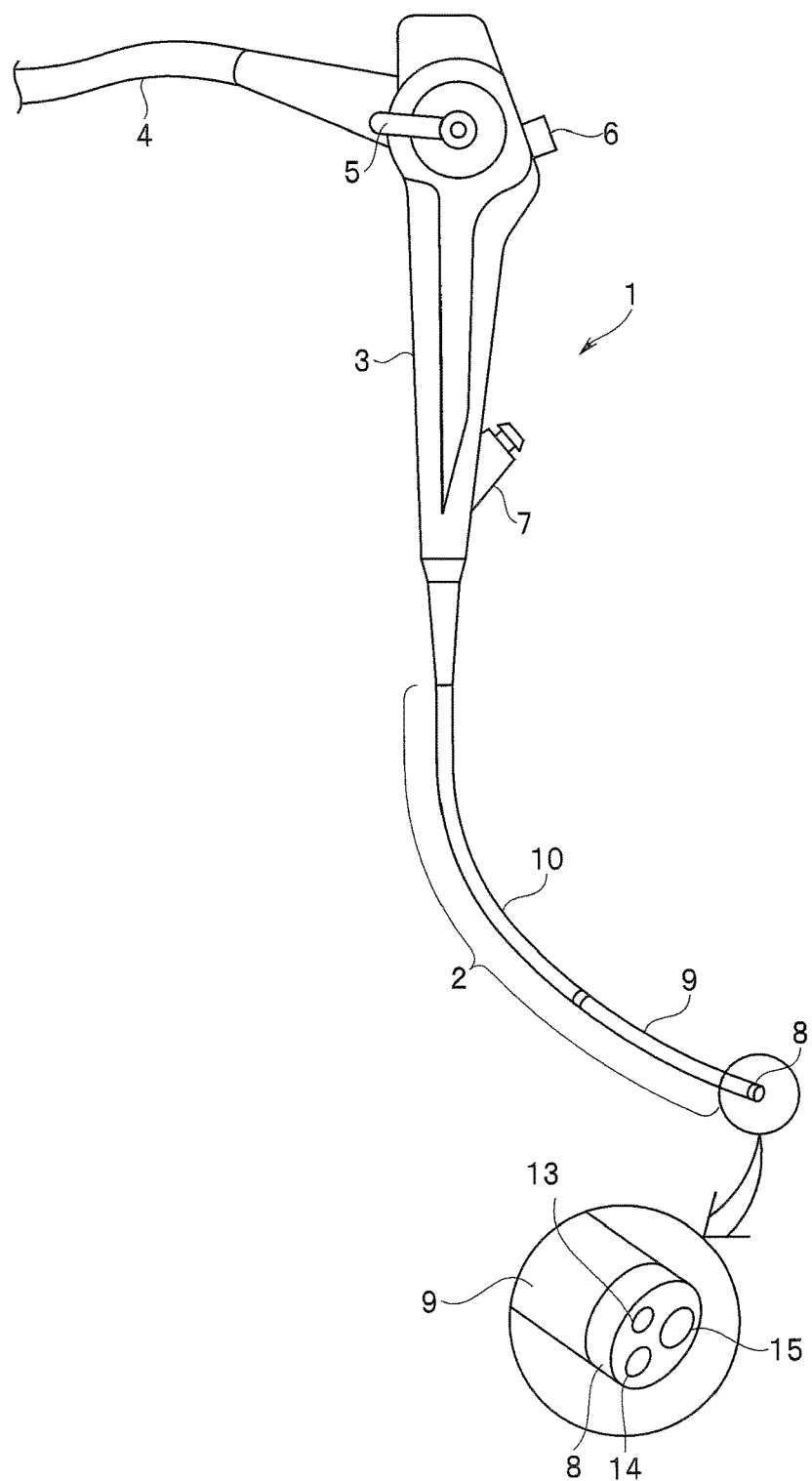
FIG. 1 is a side view of an electronic endoscope according to a first embodiment.
Figure 2:
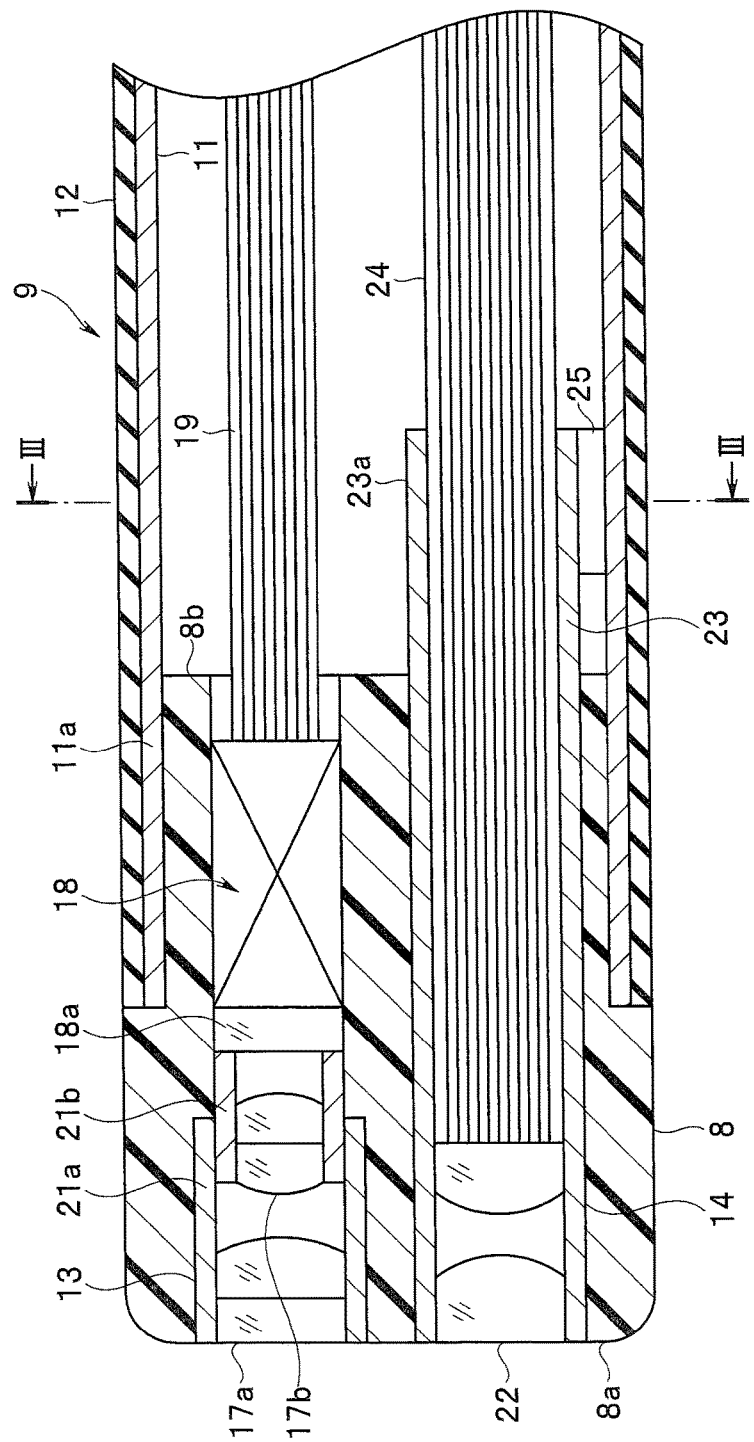
FIG. 2 is a side cross-sectional view taken along a line passing through a center between an observation window and an illumination window at a distal end portion of the endoscope, according to the first embodiment.
Figure 3:
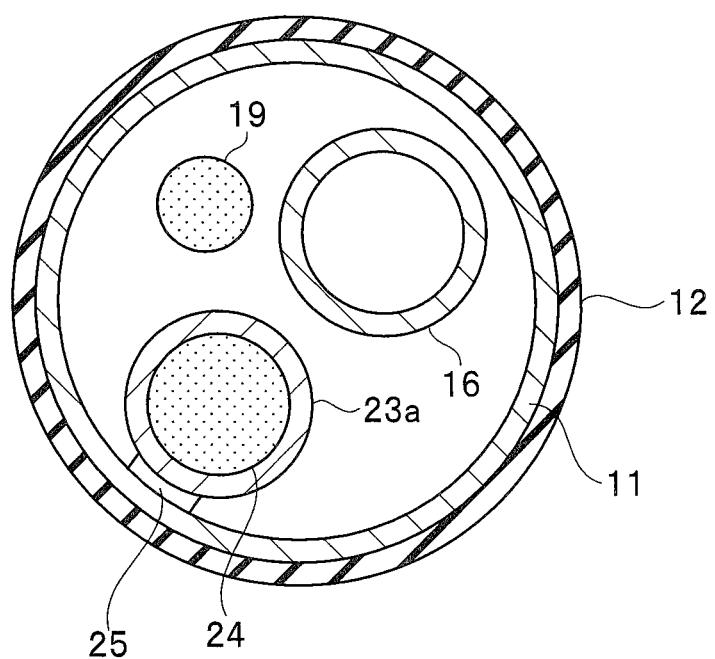
FIG. 3 is a cross-sectional view taken along line in FIG. 2, according to the first embodiment.

FIGS. 1 to 3 illustrate the first embodiment of the present invention. An electronic endoscope 1 shown in FIG. 1 is a bronchoscope, for example, and includes an insertion portion 2 to be inserted into a subject, an operation portion 3 provided on the proximal end side of the insertion portion 2, and a universal cable 4 extended from the operation portion 3.

The operation portion 3 is provided with an angle lever 5, a suction button 6, a treatment instrument insertion port 7, and the like. The angle lever 5 is used for bending a bending portion 9, to be described later, provided at the insertion portion 2 in an up direction and a down direction, for example. The treatment instrument insertion port 7 is communicated with a treatment instrument channel port 15 bored on a distal end rigid portion 8 to be described later, through a treatment instrument channel 16 (see FIG. 3) that serves also as a suction conduit disposed in the insertion portion 2, and a treatment instrument such as forceps introduced from the treatment instrument insertion port 7 passes through the treatment instrument channel 16, to be protruded forward from the treatment instrument channel port 15.

In addition, a connector (not shown) which is attachable to and detachable from a camera control unit, not shown, is provided on the proximal end side of the universal cable 4. Note that the camera control unit includes a power supply section that supplies electric power to an image pickup unit 18 to be described later and a light source (not shown) that are provided on the distal end side of the insertion portion 2, an image processing section that processes an electric signal transmitted from the image pickup unit 18 to output the processed electric signal to a display apparatus (not shown), and the like.

The insertion portion 2 includes a distal end rigid portion 8 provided at a distal end portion thereof, the bending portion 9 disposed at a proximal end portion 8b of the distal end rigid portion 8, and a flexible portion (flexible tube) 10 provided continuously with the proximal end portion of the bending portion 9. The bending portion 9 includes a bending tube 11 which is bent by the operation of the angle lever 5, and the outside of the bending tube 11 is covered with a cover tube 12.

The bending tube 11 is formed by coupling a plurality of bending pieces in an axial direction so as to be rotatable with respect to each other, and a bending piece 11a located at the front-most portion is connected and fixed to the proximal end portion 8b of the distal end rigid portion 8. In addition, inside each of the bending pieces, for example, a pair of operation wires (not shown) are inserted, and the distal end of each of the operation wires is fixed in the state being held by a wire stopper portion 11b (see FIG. 14) formed by cutting and being raised in the bending piece 11a located at the front-most portion. The proximal end side of each of the operation wires passes through the bending portion 9 and the flexible portion 10, to be coupled with the angle lever 5 provided at the operation portion 3.

Furthermore, the proximal end of the bending tube 11 and the distal end of the flexible portion 10 are connected with each other through a metallic connection pipe sleeve. The flexible portion 10 includes a flex (spiral tube) and a braid (mesh tube) disposed outside of the flex, and the outer circumference of the braid is covered with an outer tube and connected with the bending piece located at the rear-most portion through the above-described connection pipe sleeve. Each of the bending pieces including the bending piece 11a located at the front-most portion, the operation wires, the flex, and the braid are made of materials having conductivity, such as stainless steel. Furthermore, the flex and the braid are electrically connected to a circuit ground (patient GND) provided in a known patient circuit incorporated in the camera control unit through a ground wire in the universal cable 4.

In addition, the distal end rigid portion 8 having an insulation property is made of resin and formed in a cylindrical shape. The distal end rigid portion 8 includes inside thereof an observation window 13, an illumination window 14, and the treatment instrument channel port 15 that are bored in parallel with each other along the axial direction and open on the distal end portion 8a. A first objective lens barrel 21a is mounted to the observation window 13 from the distal end portion 8a side and fixed to the observation window 13, and a second objective lens barrel 21b is mounted and fixed to the proximal end side inner circumference of the first objective lens barrel 21a. Furthermore, the first objective lens barrel 21a holds a distal end side objective optical system 17a, and the second objective lens barrel 21b holds a proximal end side objective optical system 17b.

The image pickup unit 18 is mounted and fixed on the proximal end portion 8b side of the distal end rigid portion 8 so as to be located coaxially with the observation window 13. The image pickup unit 18 receives images formed by the respective objective optical systems 17a, 17b, photoelectrically converts the received images, to output the photoelectrically converted images. The image pickup unit 18 includes a cover glass 18a at the distal end thereof, and at the rear portion of the cover glass 18a, an image pickup circuit substrate on which an image pickup device that picks up formed images, such as CCD or CMOS, and a plurality of electronic components are mounted, and the like, are disposed in a predetermined manner. In addition, an image pickup electric cable 19 is extended from the image pickup circuit substrate in the proximal end direction.

The image pickup unit 18 is mounted and fixed to the distal end rigid portion 8 having the insulation property, with the front portion of the image pickup unit 18 being abutted against the second objective lens barrel 21b through the cover glass 18a, and the proximal end side of the image pickup unit 18 is housed in the distal end rigid portion 8. That is, the image pickup unit 18 is mounted insulated from the metal members located around the image pickup unit 18.

Furthermore, an illumination lens barrel 23 that holds an illumination optical system 22 constituted of a plurality of optical lenses is mounted and fixed to the illumination window 14, and further a light guide bundle 24 is mounted and fixed to the illumination lens barrel 23 from rear side of the illumination lens barrel 23. The illumination lens barrel 23 is made of a metal material such as stainless steel having relatively high conductivity, and the proximal end side of the illumination lens barrel 23 is protruded from the proximal end portion 8b of the distal end rigid portion 8, as shown in FIG. 2. Furthermore, the outer circumference of the proximal end portion 23a of the illumination lens barrel 23 and the inner circumference of the bending tube 11 such as the bending piece 11a located at the front-most portion are electrically conducted with each other by a first conductive portion 25 having conductivity.

The first conductive portion 25 may be a separate portion formed separately from the first objective lens barrel 21a and the bending tube 11, or may be formed by processing the first objective lens barrel 21a or the bending tube 11. As an example in which the first conductive portion 25 is formed as a separate portion formed separately from the first objective lens barrel 21a and the bending tube 11, it can be considered that the first conductive portion 25 is made of a solder-like or a chip-like conductive member. When a chip-like conductive member is provided as the first conductive portion 25, the conductive member is adhered with a conductive adhesive.

In such a configuration, the front face of the image pickup unit 18 is abutted, through the cover glass 18a, against the second objective lens barrel 21b linked with the first objective lens barrel 21a which is exposed to the distal end portion 8a of the distal end rigid portion 8 having an electric insulation property, and the entirety of the image pickup unit 18 is housed in the distal end rigid portion 8. As a result, the image pickup unit 18 is insulated from the metal materials located around the image pickup unit 18.

Furthermore, the illumination lens barrel 23, the distal end of which is exposed to the illumination window 14 located at the distal end rigid portion 8, has the proximal end portion 23a that is electrically conductive with the bending tube 11 through the first conductive portion 25 formed integrally with or separately from the illumination lens barrel 23. Therefore, even if the distal end rigid portion 8 is made of resin having the electric insulation property, the static electricity and high-frequency current easily flow toward the illumination lens barrel 23. The static electricity and high-frequency current flowed to the illumination lens barrel 23 passes from the first conductive portion 25 to the bending tube 11 (or the flex and braid), to be flowed to the ground through the patient GND provided in the patient circuit incorporated in the camera control unit.

As a result, the static electricity and the high-frequency current do not flow to the image pickup electric cable 19 via the image pickup unit 18, and ill effects of electricity such as noise intrusion into the image pickup unit 18 and the image pickup electric cable 19 can be effectively prevented.

Furthermore, there is no need for covering the image pickup unit 18 with a metal shield as in a conventional apparatus, which enables further size reduction of the outer diameter of the distal end portion of the endoscope. In addition, the present invention provides a simple structure in which the rear end of the illumination lens barrel 23 is only extended to be electrically connected to the bending tube 11, which prevents an increase in manufacturing costs.

Second Embodiment

FIGS. 4 to 6B show the second embodiment of the present invention. The present embodiment embodies the first conductive portion 25 in the above-described first embodiment. Therefore, the constituent elements other than the part corresponding to the first conductive portion 25 are the same as those in the first embodiment. The same constituent elements are attached with the same reference numerals and description thereof will be omitted.

Figure 5:
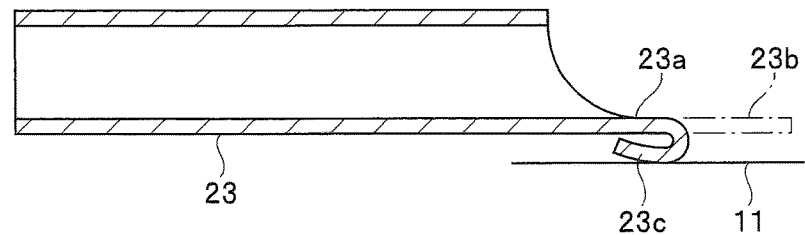
FIG. 5 is a cross-sectional side view of an illumination lens barrel according to the second embodiment.

The illumination lens barrel 23 in the present embodiment is made of a material having conductivity and a spring property, like stainless spring steel (for example, SUS304-WPB). In addition, as shown in FIG. 5, a protruding piece 23b shown with the one-dot chain line is integrally formed by cutting a part of the base portion of the illumination lens barrel 23, and a contact 23c as a first conductive portion is formed by folding back the protruding piece 23b, which is extended in the proximal end direction, outward in a curl shape. Furthermore, the contact 23c has a height so that the contact 23c is easily pushed into a gap between the outer circumference of the illumination lens barrel 23 and the inner circumference of the bending tube 11.

Figure 4:
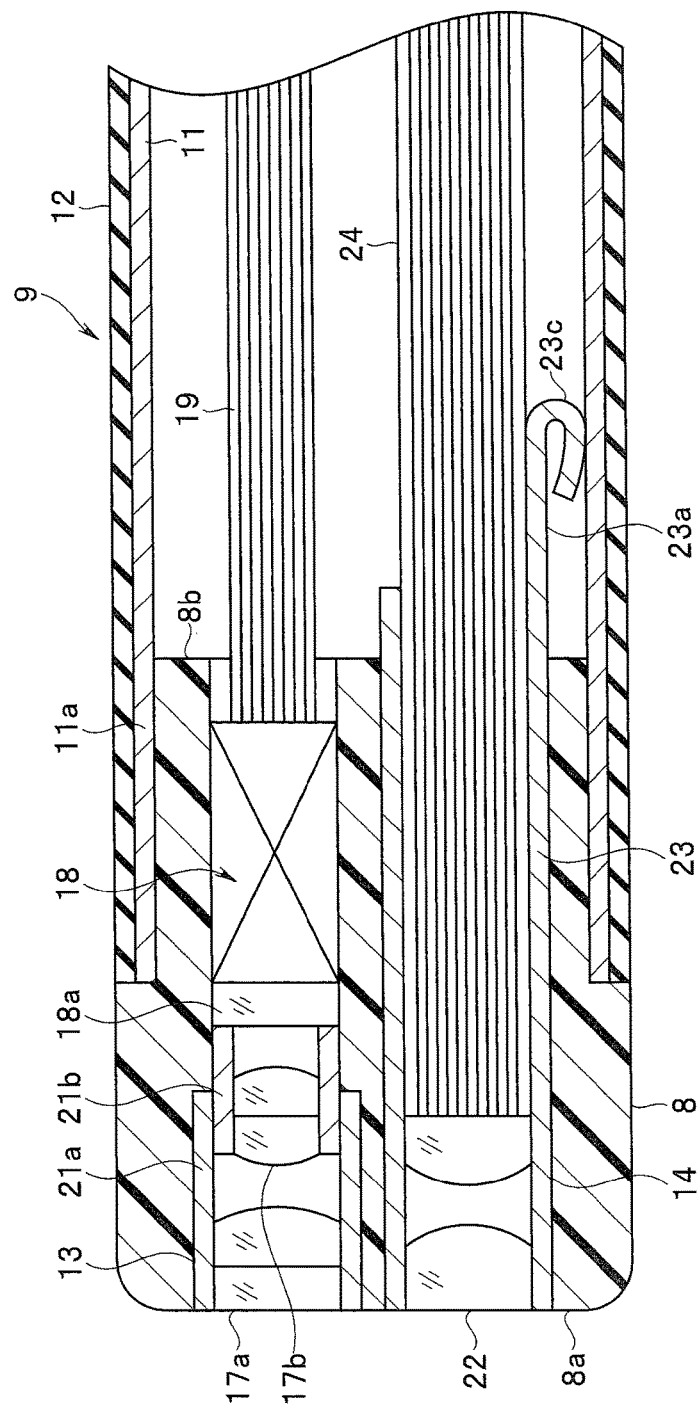
FIG. 4 is a cross-sectional view corresponding to FIG. 2 according to a second embodiment.

Therefore, as shown in FIG. 4, in the state where the illumination lens barrel 23 is mounted and fixed to the illumination window 14 bored at the distal end rigid portion 8, the contact 23c is abutted against the inner circumference of the bending tube 11. The contact 23c has the height set such that the contact 23c can be easily pushed into the gap between the outer circumference of the illumination lens barrel 23 and the inner circumference of the bending tube 11 and the contact 23c is made of the spring steel having conductivity. Therefore, the contact 23c is constantly abutted against the inner circumference of the bending tube 11 with a predetermined surface pressure being maintained.

As a result, the static electricity and the high-frequency current flowed to the illumination lens barrel 23 can be flowed toward the bending tube 11 via the contact 23c. In addition, in this case, plating processing is applied to the contact 23c with a material having high conductivity such as gold plating, thereby capable of obtaining excellent conductivity.

In addition, in the present embodiment, the contact 23c formed at the illumination lens barrel 23 is abutted against the bending tube 11. In such a structure, the distal end rigid portion 8 can be easily detached from the bending portion 9 for maintenance, and after that, the distal end rigid portion can be easily attached to the bending portion 9, which enables an excellent maintenance performance to be obtained. Furthermore, the illumination lens barrel 23 is made of spring steel, which causes less fatigue of the illumination lens barrel even if attachment and detachment of the distal end rigid portion 8 are repeated for each maintenance operation and provides an excellent durability.

Figure 6A:
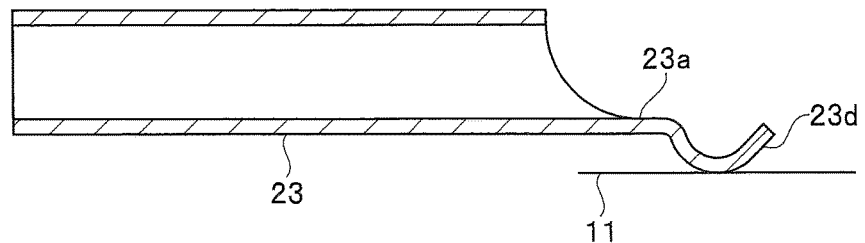
FIG. 6A is a cross-sectional side view of an illumination lens barrel according to another aspect of the second embodiment.
Figure 6B:
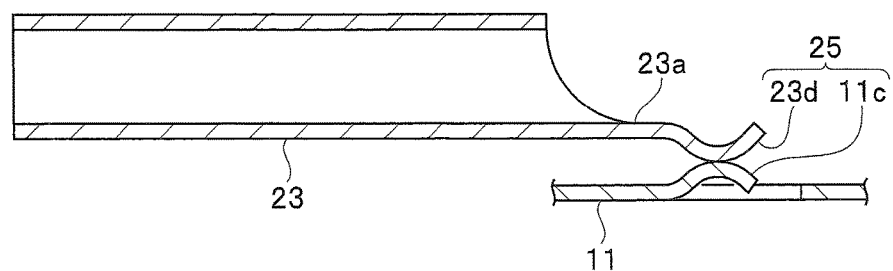
FIG. 6B is a cross-sectional side view of an illumination lens barrel and a bending tube according to yet another aspect of the second embodiment.

The above-described contact 23c is formed by folding back the protruding piece 23b. However, as shown in FIG. 6A, a contact 23d that is convexly bent in the inner circumferential direction of the bending tube 11 may be used. Furthermore, as shown in FIG. 6B, a contact receiving portion 11c bent convexly toward the contact 23d is formed by cutting and being raised at a position opposed to the contact 23d and the contact 23d and the contact receiving portion 11c may be abutted against each other to establish conduction therebetween. The bending tube 11 includes the contact receiving portion 11c, thereby enabling the contact 23d to be abutted against the contact receiving portion 11c at a relatively high pressure. As a result, higher conductivity can be obtained. In this case, the contact 23d corresponds to the first contact of the present invention, and the contact receiving portion 11c corresponds to the second contact of the present invention. Furthermore, the contact 23d and the contact receiving portion 11c configure the first conductive portion 25.

Third Embodiment

FIGS. 7 to 10 show the third embodiment of the present invention. In the above-described second embodiment, conductivity is ensured by bringing the contacts 23c, 23d formed at the illumination lens barrel 23 into contact with the inner circumference of the bending tube 11. In the present embodiment, the bending tube 11 includes a contact 11e (11f, 11g), as a first conductive portion. Note that the present embodiment embodies the first conductive portion 25 in the first embodiment, and other constituent elements are the same as those in the first embodiment. The same constituent elements are attached with the same reference numerals and description thereof will be omitted.

Figure 7:
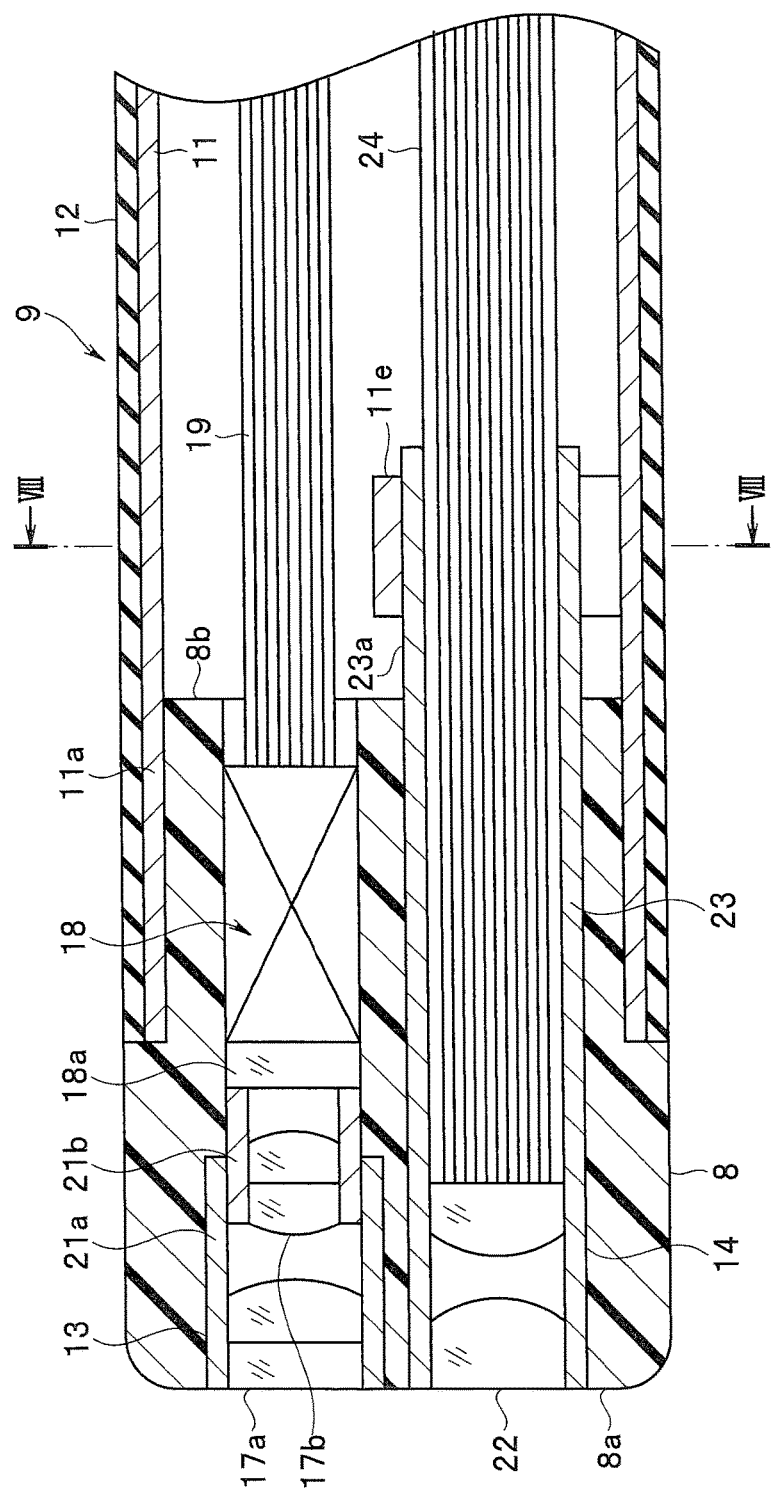
FIG. 7 is a cross-sectional view corresponding to FIG. 2 according to a third embodiment.
Figure 8:
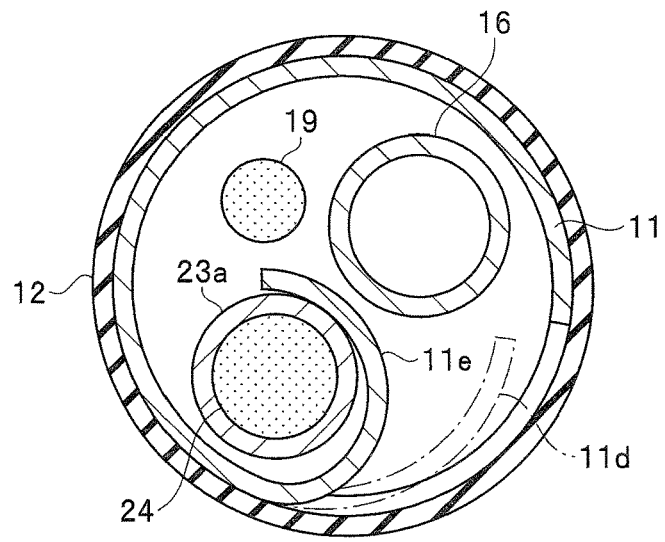
FIG. 8 is a cross-sectional view taken along line VIII-VIII in FIG. 7, according to the third embodiment.

The bending tube 11 in the present embodiment is made of a material having conductivity and a spring property, like a stainless spring steel (for example, SUS304-WPB). That is, as shown in FIGS. 7 and 8, a cut-and-raised portion 11d is integrally formed along the circumferential direction on the side surface of the bending tube 11 opposed to the proximal end portion 23a of the illumination lens barrel 23, as shown with the one-dot chain line in FIG. 8, and the cut-and-raised portion 11d is bent inward to be extended, to thereby form the contact 11e that is surface-abutted against the outer circumference of the illumination lens 23 by a spring pressure.

In the present embodiment, the bending tube 11 is provided with the contact 11e formed bent so as to be surface-abutted against the outer circumference of the illumination lens barrel 23, which enables the illumination lens barrel 23 to have a substantially cylindrical shape. As a result, the structure can be simplified. In addition, the outer diameter of the bending tube 11 is larger than the outer diameter of the illumination lens barrel 23, thereby enabling an excellent processing performance to be obtained. Furthermore, the contact 11e is configured to be wound around the outer circumference of the illumination lens barrel 23. Such a configuration allows the abutting area to be increased, to enable an excellent conductivity to be obtained. Furthermore, the contact 11e is surface-abutted against the outer circumference of the illumination lens barrel 23 only by the spring pressure. Therefore, the distal end rigid portion 8 can be easily inserted into and extracted from the bending portion 9 for maintenance, which is capable of providing an excellent workability.

Figure 9:
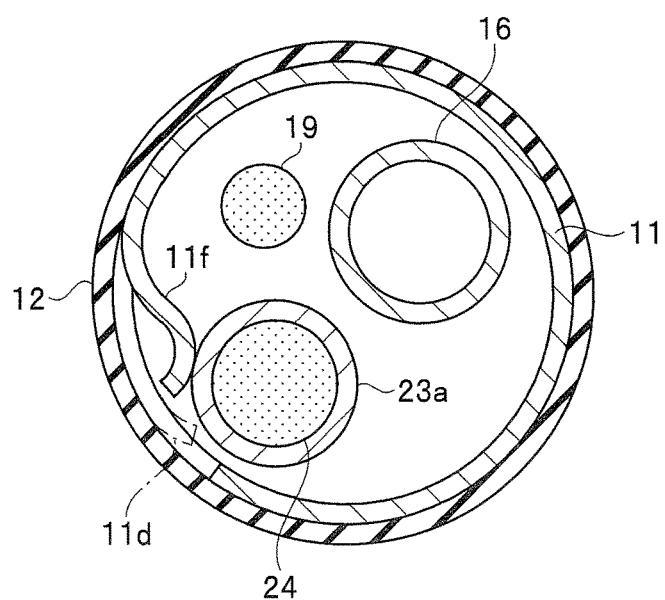
FIG. 9 is a cross-sectional view corresponding to FIG. 8 according to another aspect of the third embodiment.

In this case, as shown in FIG. 9, for example, the cut-and-raised portion 11d formed in the bending tube 11 may be processed in a convexly bent shape so as to be pressed against the outer circumference of the illumination lens barrel 23, to form the contact 11f. The processing performance of the contact 11f shown in FIG. 9 is more excellent than that of the contact 11e shown in FIG. 8 that is formed by bending the cut-and-raised portion 11d so as to be wound around the illumination lens barrel 23.

Figure 10:
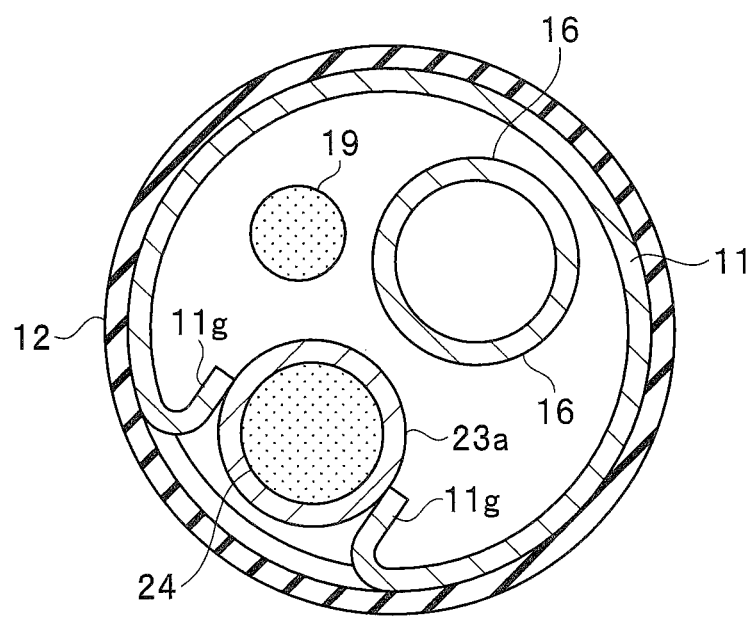
FIG. 10 is a cross-sectional view corresponding to FIG. 8 according to yet another aspect of the third embodiment.

Furthermore, as shown in FIG. 10, the cut-and-raised portion 11d formed in the bending tube 11 is divided into two parts in the circumferential direction, and the respective two parts are bent in the inner circumferential direction to form a pair of contacts 11g, 11 g that sandwich the outer circumference of the illumination lens barrel 23 from both sides thereof to abut against the outer circumference of the illumination lens barrel 23.

Fourth Embodiment

Figure 11:
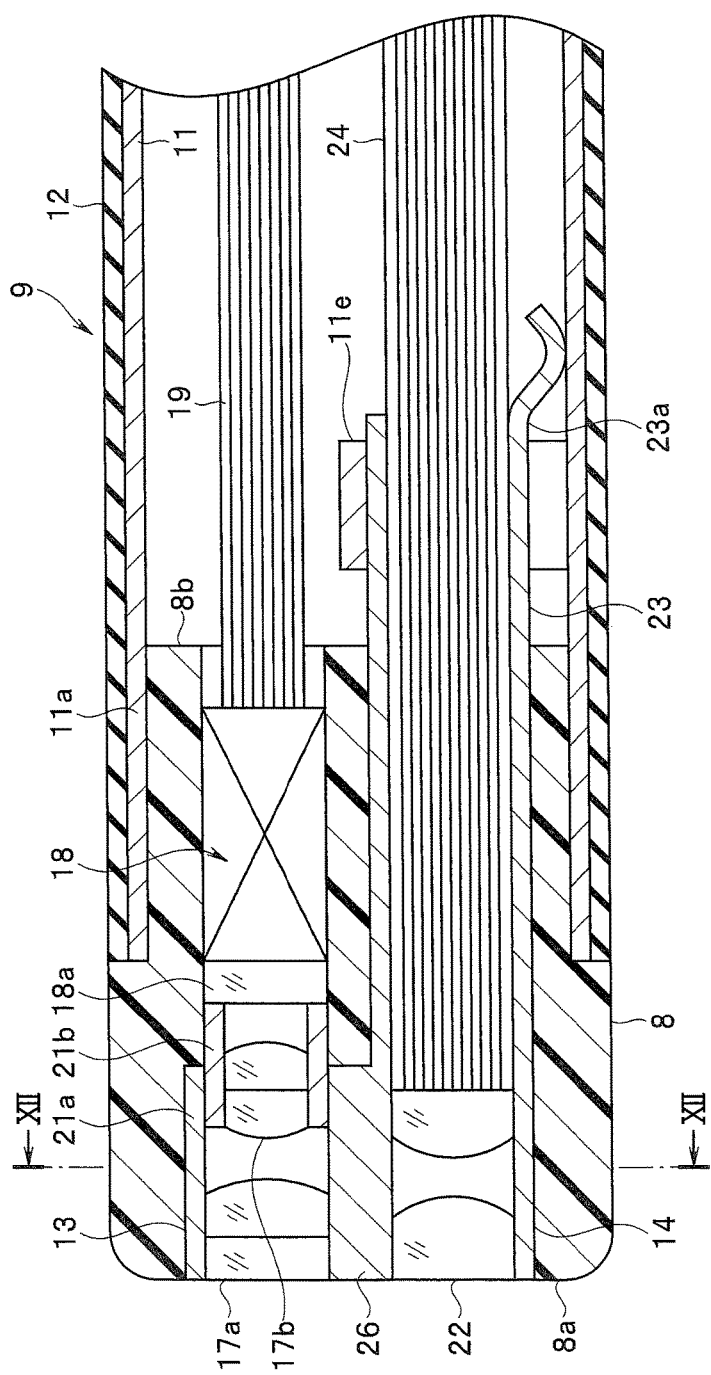
FIG. 11 is a cross-sectional view corresponding to FIG. 2, according to a fourth embodiment.
Figure 12:
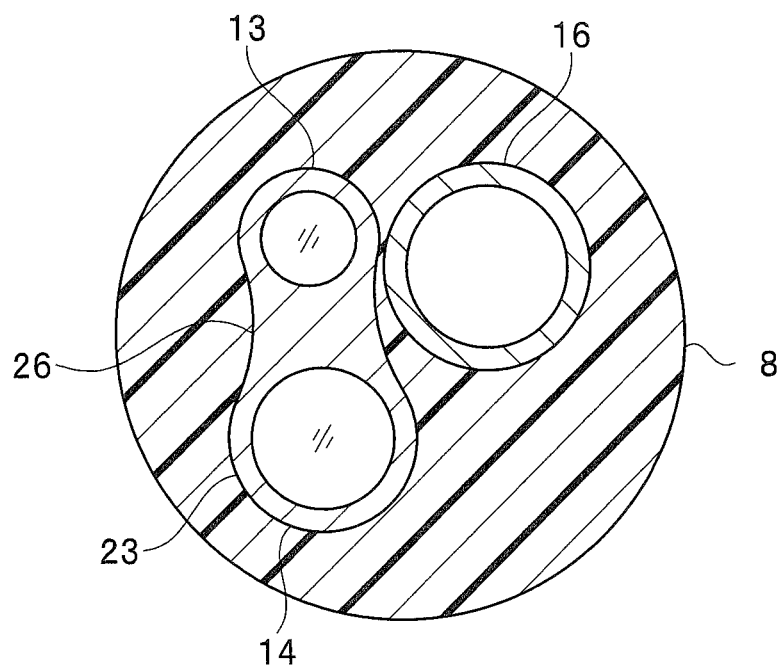
FIG. 12 is a cross-sectional view taken along line XII-XII in FIG. 11, according to the fourth embodiment.

FIGS. 11 and 12 show the fourth embodiment of the present invention. In the present embodiment, the contact 23d shown in the second embodiment is formed at the illumination lens barrel 23, and the contact 11e shown in the third embodiment is formed in the bending tube 11.

The illumination lens barrel 23 and the bending tube 11 are abutted against each other both with the contact 23d formed at the illumination lens barrel 23 and the contact 11e formed in the bending tube 11, which enables higher conductivity to be obtained.

Furthermore, in the present embodiment, the illumination lens barrel 23, which is a first lens barrel, made of a metal material having conductivity and a first objective lens barrel 21a as a second lens barrel are integrated through a continuous portion 26 as a second conductive portion. In addition, a second objective lens barrel 21b as a third lens barrel is made of an insulating material such as metallic glass having a high resistance value.

The first objective lens barrel 21a and the illumination lens barrel 23 that have conductivity are integrated through the continuous portion 26, and the second objective lens barrel 21b is made of the insulating material, thereby capable of reducing the electric resistance between the integrated illumination lens barrel 23 and first objective lens barrel 21a and the bending tube 11 more remarkably than the electric resistance between the integrated illumination lens barrel 23 and first objective lens barrel 21a and the image pickup unit 18.

As a result, even if strong static electricity or high-frequency current is applied to the first objective lens barrel 21a, for example, the static electricity or the high-frequency current can be surely flowed to the patient GND through the illumination lens barrel 23, which enables intrusion of noise to the image pickup unit 18 to be effectively prevented.

The first objective lens barrel 21a and the illumination lens barrel 23 do not have to be formed integrally, but may be integrated by adhering the barrels to each other with a conductive adhesive. When adhering the barrels to each other, if an adhesive bank penetrating the observation window 13 and the illumination window 14 is formed between the windows 13 and 14 that are bored on the distal end rigid portion 8 made of resin, and adhesive is injected into the adhesive bank to adhere the first objective lens barrel 21a and the illumination lens barrel 23 with each other later, the workability is improved. Alternatively, a metallic plate spring may be mounted to the adhesive bank to establish conduction between the first objective lens barrel 21a and the illumination lens barrel 23, to integrate the first objective lens barrel 21a and the illumination lens barrel 23 by applying a conductive adhesive. In this case, the conductive adhesive and the metallic plate spring correspond to the second conductive portion of the present invention.

Fifth Embodiment

Figure 13:
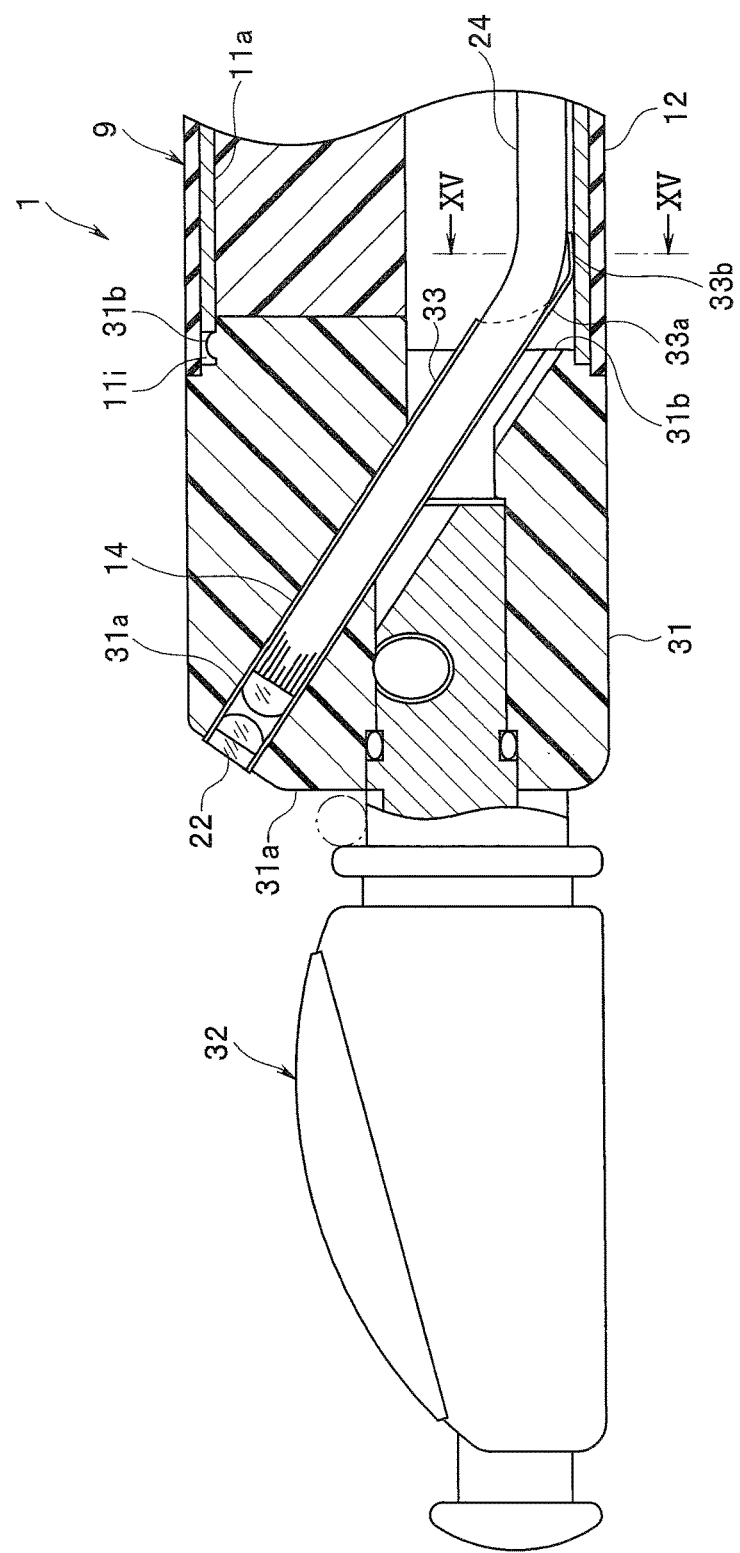
FIG. 13 is a partial cross-sectional side view of a distal end of an ultrasound endoscope according to a fifth embodiment.

FIGS. 13 to 16 show the fifth embodiment of the present invention. As shown in FIG. 13, an electronic endoscope 1 according to the present embodiment is an ultrasound endoscope having an oblique-view optical system, and an ultrasound transducer unit 32 is attached to a distal end portion 31a of a distal end rigid portion 31 made of resin having an electric insulation property. In addition, an illumination window 31a is open at an upper portion of the distal end rigid portion 31. Note that, though not shown, an observation window to which an objective lens barrel that holds an objective optical system is mounted is open in parallel with the illumination window 31a.

The illumination window 31a is bored obliquely downward in the direction from the distal end portion 31a to the proximal end portion 31b of the distal end rigid portion 31. An illumination lens barrel 33 that holds an illumination optical system 22 and has conductivity and spring property is inserted and fixed in the illumination window 31a. The proximal end portion of the illumination lens barrel 33 is protruded to be extended from the proximal end portion 31b of the distal end rigid portion 31, and the proximal end portion 31b is abutted against the bending piece 11a provided at the front-most portion of the bending tube 11.

Figure 14:
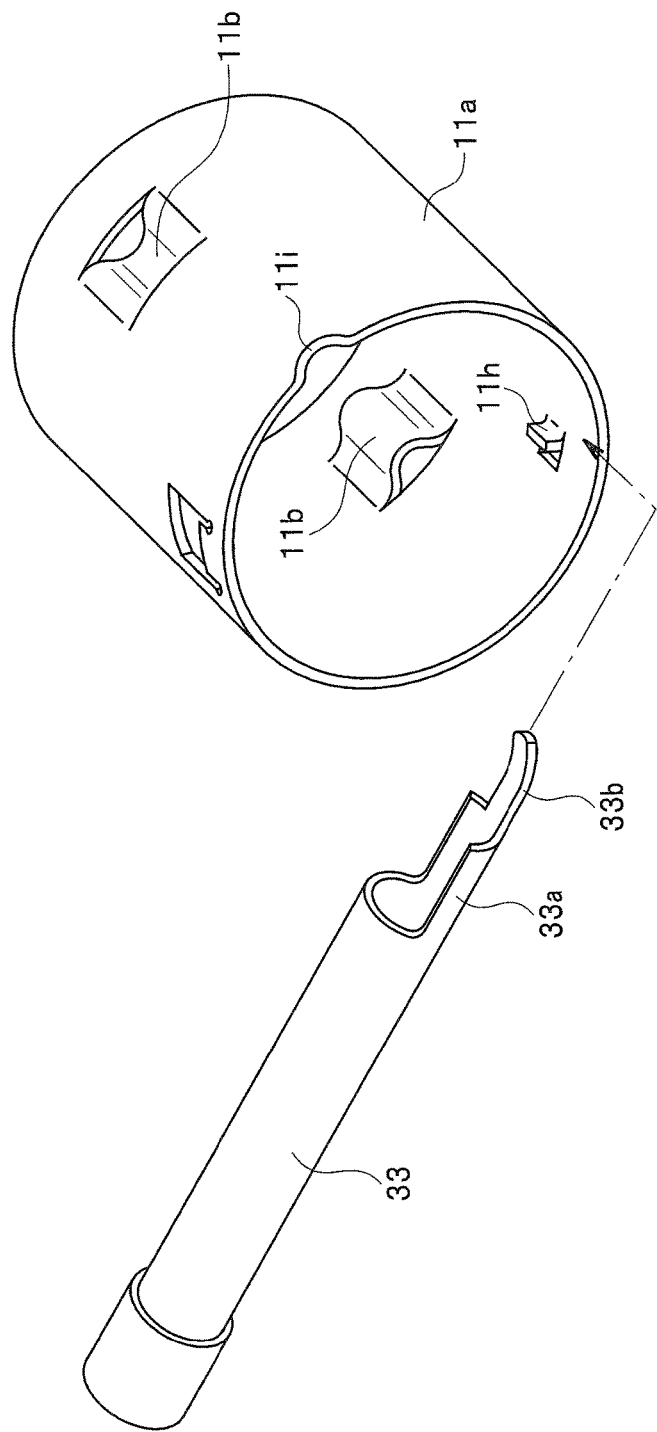
FIG. 14 is a perspective view of an illumination lens barrel and a bending tube according to the fifth embodiment.

As shown in FIG. 14, the proximal end portion 33a of the illumination lens barrel 33 is cut out such that a light guide bundle 24, which extends in the distal end direction from the base portion side on which the operation portion of the electronic endoscope 1 is provided, is inserted into the illumination lens barrel 33. At the rear end portion of the proximal end portion 33a, a first contact 33b is integrally formed in a protruded manner.

The first contact 33b is configured to be abutted against the inner surface of the bending piece 11a, and flexed so as to be in parallel with the bending piece 11a, as shown in FIG. 13. On the other hand, as shown in FIGS. 14 and 15A, a second contact 11h is cut and raised in the bending piece 11a. The second contact 11h has a cut-and-raised surface protruded so as to abut against a side surface of the first contact 33b formed integrally with the illumination lens barrel 33. The first contact 33b is abutted against the second contact 11h, thereby establishing conduction between the first contact and the second contact, and the first conductive portion 25 is configured, with the first contact 33b and the second contact 11h being brought into contact with each other.

In addition, as shown in FIG. 14, a positioning hole portion 11i is formed in a semicircular shape at the front end of the bending piece 11a. A protruding portion 31b that is engaged with the positioning hole portion 11i is formed on the outer circumference of the distal end rigid portion 31. Note that the reference numeral 11b of the bending piece 11a indicates a wire stopper portion that retains the distal end of the operation wire (not shown).

In such a configuration, the proximal end portion 31b of the distal end rigid portion 31 to which the ultrasound transducer unit 32, the illumination lens barrel 33 that holds the illumination optical system 22, and the objective lens barrel (not shown) that holds the objective optical system are fixed in advance is first fitted to the inner circumference of the bending piece 11a provided at the front-most portion of the bending tube 11. As a result, the first contact 33b formed at the proximal end portion 33a of the illumination lens barrel 33 is abutted against the inner circumference of the bending piece 11a.

Figure 15:
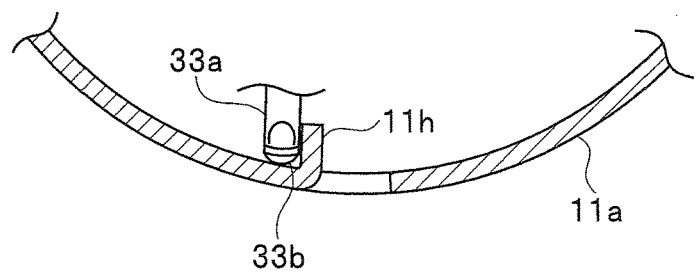
FIG. 15 is a cross-sectional view showing an abutting state between a first contact formed at an illumination lens and a second contact formed in the bending tube, according to the fifth embodiment.

After that, the distal end rigid portion 31 is rotated in the axial direction to allow the protruding portion 31b formed on the outer circumference of the proximal end portion of the distal end rigid portion 31 to engage with the positioning hole portion 11i formed at the front end portion of the bending piece 11a. Then, as shown in FIG. 15, the side surface of the first contact 33b is abutted against the second contact 11h cut and raised in the bending piece 11a. As a result, the first contact 33b is conductive both with the inner circumference of the bending piece 11a and the second contact 11h.

Thus, in the present embodiment, even if the illumination lens barrel 33 is fixed to the distal end rigid portion 31 in the obliquely inclined state, the first contact 33b is abutted against the bending piece 11a, to thereby capable of bringing the illumination lens barrel 33 into the conductive state only by mounting the distal end rigid portion 31 to the bending piece 11a. Therefore, special components and working are not necessary for the electrical conduction between the illumination lens barrel 33 and the bending tube 11a, which provides an excellent workability. Furthermore, the second contact 11h formed in the bending piece 11a has only to be processed together with the existing wire stopper portion 11b and the like, which enables an increase in manufacturing man-hours to be prevented.

Figure 16A:
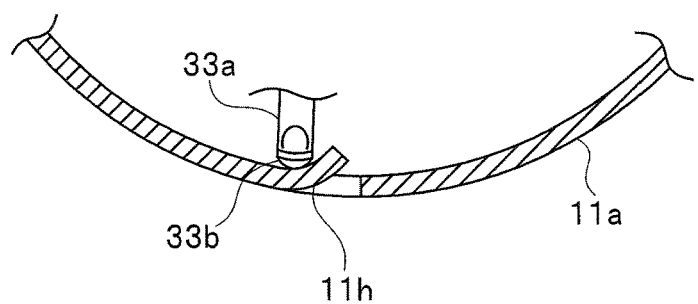
FIG. 16A is a cross-sectional view corresponding to FIG. 15 according to another aspect of the fifth embodiment.
Figure 16B:
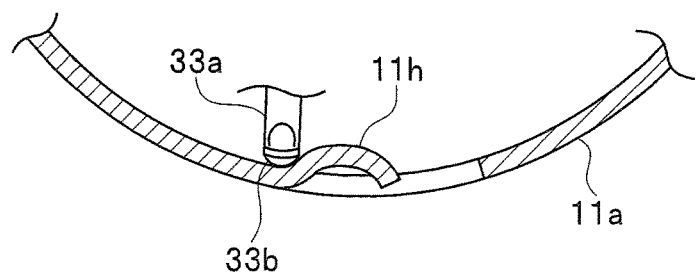
FIG. 16B is a cross-sectional view corresponding to FIG. 15 according to yet another aspect of the fifth embodiment.

The second contact 11h may be formed to be bent inward as shown in FIG. 16A, or convexly bent inward as shown in FIG. 16B. Since the second contact 11h is bent, spring pressure can be generated when the first contact 33b is abutted against the second contact 11h, which is capable of providing more secure conductivity.

What is claimed is:
1. An endoscope comprising:
an insertion portion to be inserted into a subject;
a distal end rigid portion including a distal end portion and a proximal end portion, the distal end rigid portion being made of resin and provided at a distal end portion of the insertion portion;
a bending tube made of metal and provided continuously with the distal end rigid portion;
an illumination optical system provided at the distal end rigid portion;
a first lens barrel made of metal and extended in a direction of the proximal end portion;
an objective optical system provided at the distal end rigid portion and including a distal end side objective optical system and a proximal end side objective optical system;
an image pickup sensor that picks up an image formed by the objective optical system;
a second lens barrel made of metal that holds the distal end side objective optical system, the second lens barrel being electrically conductive with the first lens barrel;
a first conductive material that establishes electrical conduction between the bending tube and the first lens barrel; and
a third lens barrel that holds the proximal end side objective optical system and the image pickup sensor, the third barrel being made of a material having an electric resistance value higher than electric resistance values of the first lens barrel and the second lens barrel.
2. The endoscope according to claim 1, wherein the first conductive material is a contact formed integrally with a proximal end portion of the first lens barrel and extended so as to be abutted against the bending tube.
3. The endoscope according to claim 1, wherein the first conductive material is a contact formed integrally on a side surface of the bending tube and extended so as to be abutted against the first lens barrel.
4. The endoscope according to claim 3, wherein the contact is formed to be bent so as to be wound around an outer circumference of the first lens barrel.
5. The endoscope according to claim 1, wherein the first lens barrel and the second lens barrel are formed integrally.
6. The endoscope according to claim 1, wherein the first lens barrel and the second lens barrel are electrically conductive with each other through a second conductive material.
7. The endoscope according to claim 1, wherein
the first conductive material comprises:
a first contact formed integrally with a proximal end portion of the first lens barrel and protruded toward the bending tube; and
a second contact formed integrally with the bending tube and protruded toward the first lens barrel, wherein the first contact and the second contact are abutted against each other, to be electrically conductive with each other.

* * * * *